United States Patent [19]

Auburn

[11] 4,428,374
[45] Jan. 31, 1984

[54] UMBILICAL CORD CLAMPING ASSEMBLY

[76] Inventor: Robert M. Auburn, 2683 Surfrider Ave., Ventura, Calif. 93003

[21] Appl. No.: 168,656

[22] Filed: Jul. 11, 1980

Related U.S. Application Data

[63] Continuation-in-part of Ser. No. 973,006, Dec. 20, 1978, abandoned, which is a continuation-in-part of Ser. No. 777,358, Mar. 14, 1977, abandoned.

[51] Int. Cl.³ .................... A61B 17/12; A61B 17/32
[52] U.S. Cl. .................................. 128/318; 128/325; 128/346
[58] Field of Search .............. 128/346, 325, 326, 305, 128/318

[56] References Cited

U.S. PATENT DOCUMENTS

| | | | |
|---|---|---|---|
| 2,052,870 | 9/1936 | Coco | 128/346 |
| 2,060,724 | 11/1936 | Carroll | 128/318 |
| 2,524,337 | 10/1956 | Whittaker | 128/346 X |
| 3,106,919 | 10/1963 | Churchville | 128/346 |
| 3,166,071 | 1/1965 | Mayer | 128/346 X |
| 3,175,556 | 3/1965 | Wood et al. | 128/346 X |
| 4,026,294 | 5/1977 | Mattler | 128/346 X |

Primary Examiner—Michael H. Thaler
Attorney, Agent, or Firm—Jack C. Munro

[57] ABSTRACT

An umbilical cord clamping assembly which in its first embodiment provides for an umbilical cord clamp which is constructed of a pair of spaced-apart clamping members connected by a connecting member. A clamping tool is provided which cooperates with the umbilical cord clamp of this invention which simultaneously causes each clamping member of the umbilical cord clamp to be installed upon the umbilical cord while also cutting of the umbilical cord therebetween and also cutting of the connecting member connecting the pair of clamping members. The second embodiment of this invention employs a pair of nonconnected clamping members which are each cradled separately in the clamping tool within a separate spring member. The spring member functions to locate the tool in the open position as well as to accommodate bowing of the clamping members about an unbilical cord. When the clamping tool is completely closed, it becomes locked which must be then deactivated to open the tool. A modification of this second embodiment relates to the using of a special form of clamp which interlocks with the spring member.

3 Claims, 16 Drawing Figures

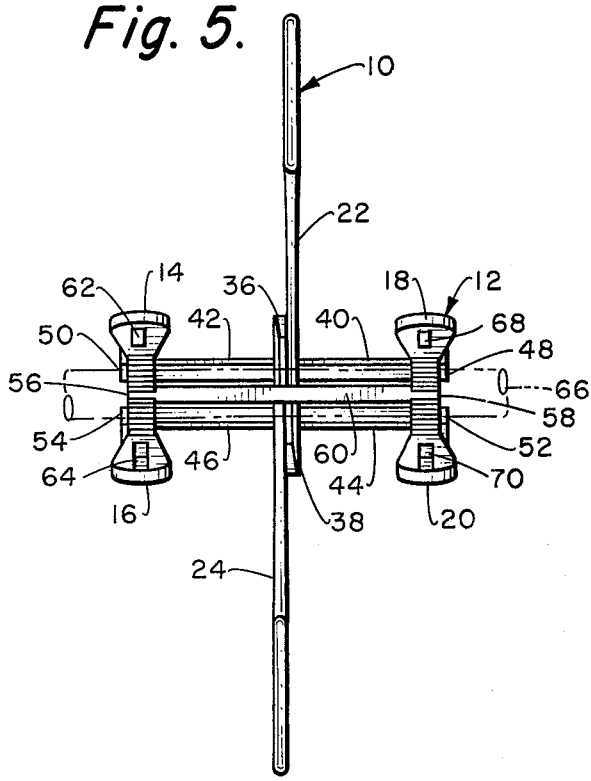
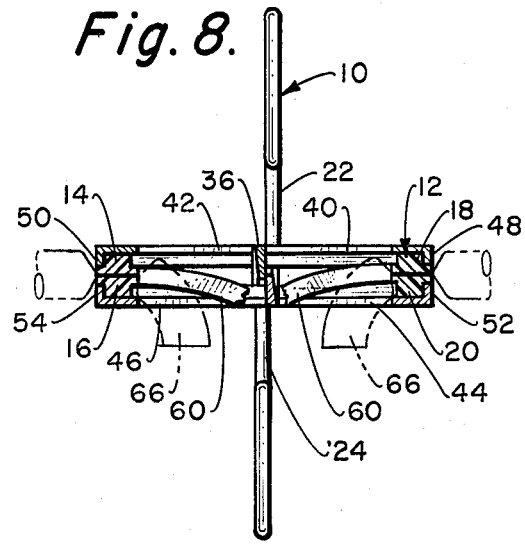
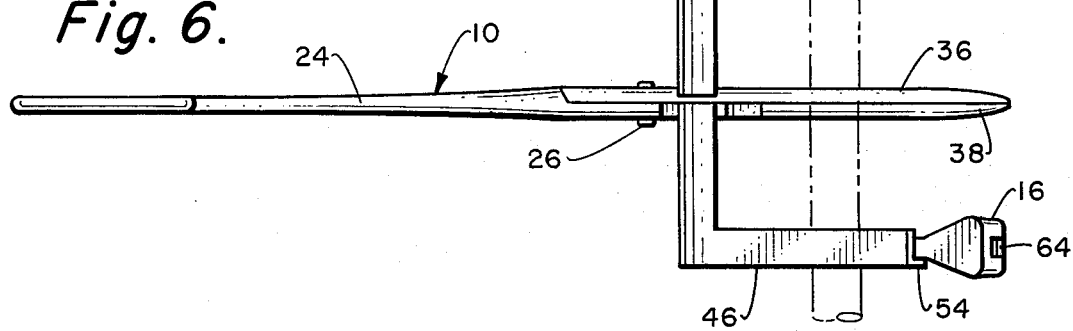
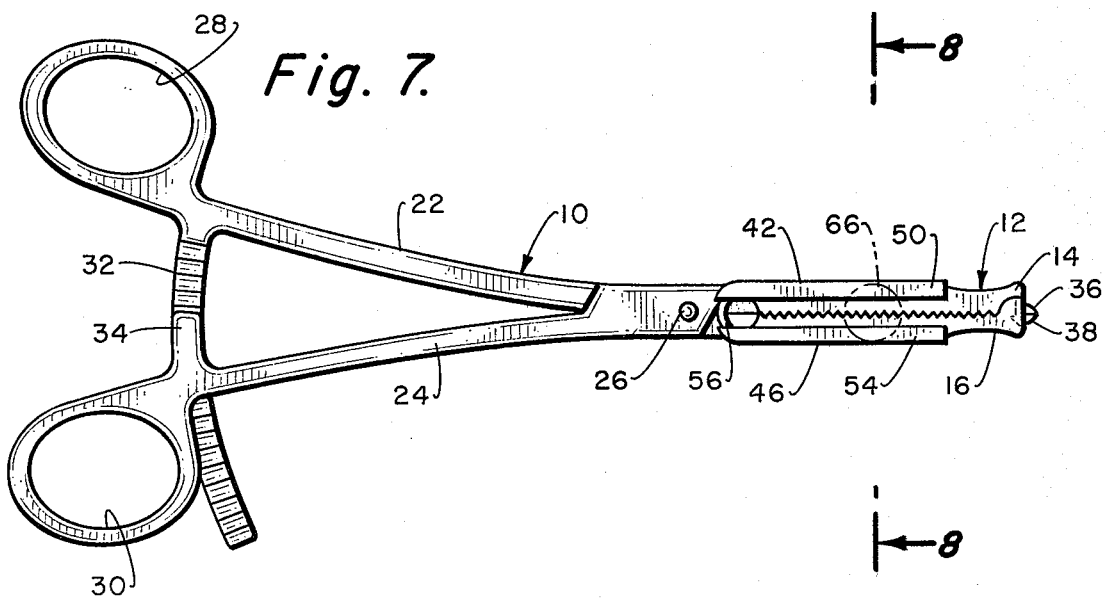

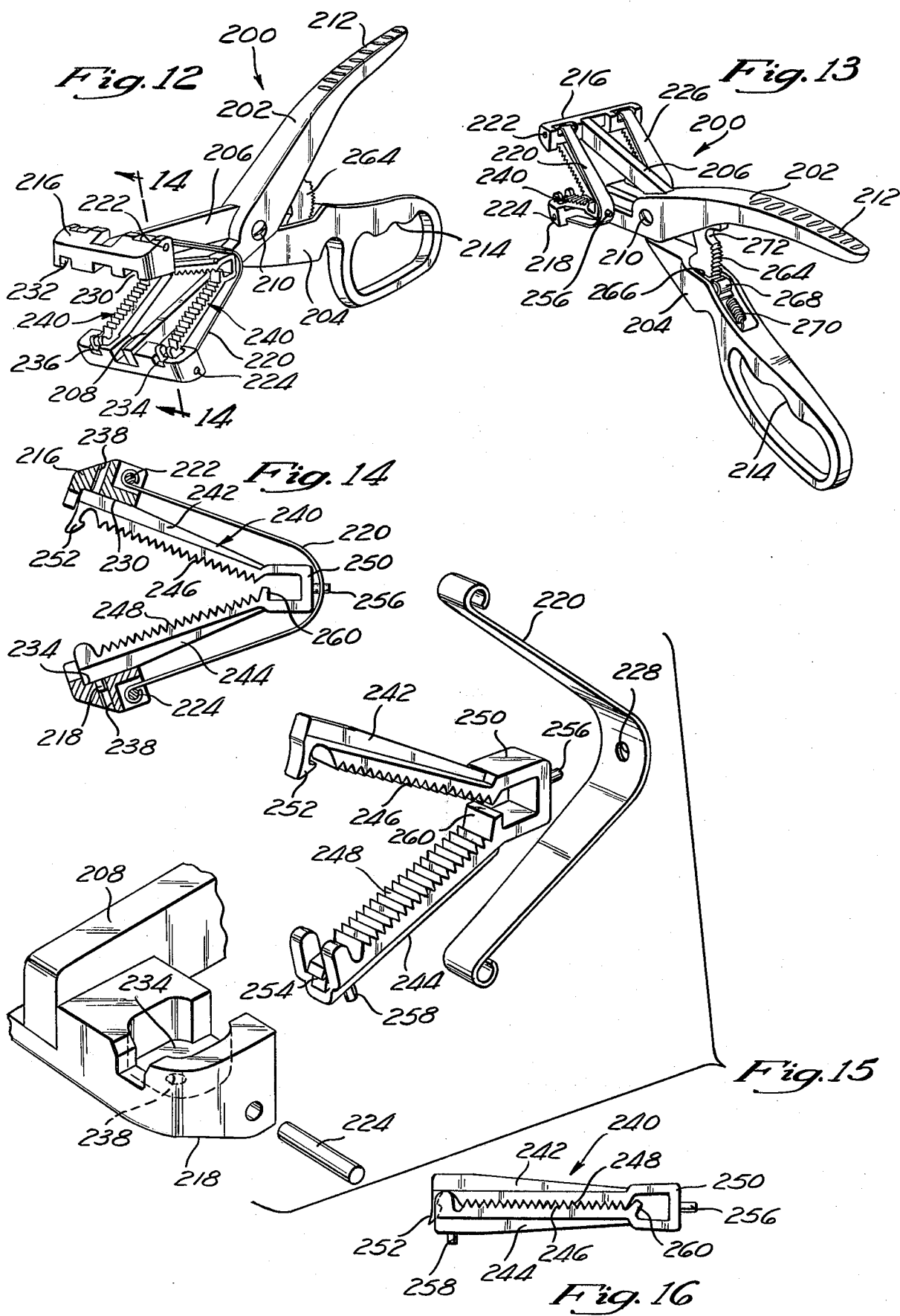

UMBILICAL CORD CLAMPING ASSEMBLY

REFERENCE TO PRIOR APPLICATION

This application is a continuation-in-part of patent application Ser. No. 973,006, filed Dec. 20, 1978, now abandoned, by the same title, which in turn was a continuation-in-part of patent application Ser. No. 777,358, filed Mar. 14, 1977, now abandoned, also by the same title, and by the same inventor.

BACKGROUND OF THE INVENTION

The field of this invention relates to a clamping assembly and more particularly to a clamping assembly for use in clamping the umbilical cord of a newborn infant.

It has been common practice for generations to cut the umbilical cord of a newborn infant and then tie off the end of the umbilical cord by a tie string. Recently, it has been common practice to employ some type of a clamp to close the end of the umbilical cord thereby eliminating the need of the tie string. Previously, a common type of such a cord clamp has been made of surgical steel and although they serve quite efficiently to close the cord, such clamps are heavy and therefore normally are required to be taped to the body of the infant in order to avoid traction on the cord. Such metallic cord clamps are rather expensive and are therefore reusable and require cleaning and sterilization prior to reuse. Therefore, the use of such a cord clamp requires the services of hospital personnel, as well as the use of hospital cleaning and sterilization equipment.

Recently, there has been in common use a lightweight umbilical cord clamp formed of plastic material. Such plastic clamps are comparatively inexpensive and are disposable, thereby eliminating the need for cleaning and sterilization. The lightweight clamp exerts little or no traction on the umbilical cord and the use of taping the umbilical cord to the body of the infant is not necessary.

The umbilical cord clamp is installed immediately after birth. This means that the physician doing the installation, with his gloved hands covered with blood and other matter, must grasp the small lightweight clamp, place such upon the cord, and push the ends of the clamp together thereby fastening such in the closed position. This procedure is repeated twice with two clamp members being located in a spaced-apart manner. The umbilical cord is then severed between the clamps with one portion of the umbilical cord remaining with the mother and the other portion of the umbilical cord being attached to the infant.

There is substantial difficulty for the physician to install these clamps since the physician's hands are quite slippery. Frequently, the clamps slip from the physician's hands. There is a definite need for a clamping assembly to facilitate quick and easy installing of such umbilical cord clamps anticipating that the installation of such clamps will be at a time when the hands of the physician are in a quite slippery condition.

SUMMARY OF THE INVENTION

The umbilical cord clamping assembly of the first embodiment of this invention provides for a clamp which comprises a first set of arms and a second set of arms. Both said sets of arms are located in substantially a V-shape with the arms of each set being connected together by an integral plastic loop at the apex. The free end of each set of arms includes a fastening means so that when the clamp is in the closed position, the clamp is locked in that position. The loops of each set of arms are connected together by a thin strip of plastic material. The clamp is to be connectable with a clamping tool which takes the form of a pair of scissors, the head of which includes a pair of spaced-apart members. One of said members of said clamping tool is to connect with said first set of arms with the other of said members of said clamping tool to connect with said second set of arms. By operation of said tool in a scissors-like motion, the sets of arms can be moved from an open position to a closed position. The tool also includes a pair of shearing members similar to a conventional scissors. Therefore, as the clamping tool is moved to the closed position, simultaneously along with each set of arms being installed upon the umbilical cord, the umbilical cord, as well as the member connecting the sets of arms, are severed, thereby accomplishing the severing of the umbilical cord as well as clamping each severed end of the umbilical cord.

The second embodiment of the umbilical cord clamping assembly of this invention is to employ the use of a pair of separate clamp members which have not been connected as in the first embodiment. Each clamp member is to be cradled within a spring member of the clamping tool with these spring members being similar to the pair of spaced-apart members of the first embodiment. With separate clamps in the open position, the spring members tightly retain the clamps within the clamping tool and prevent accidental disassociation therefrom. One purpose of the spring members is to accommodate deformation or bowing of the clamps when installed upon an umbilical cord. Another function of the spring members is to exert a continuous bias upon the tool to locate such in the open position. Operation of the second embodiment of the tool of this invention is in precisely the same manner as the first embodiment with the second embodiment also including a pair of shearing members. With the tool completely closed and the clamp members tightly clamped about the umbilical cord, the clamping tool becomes locked by locking means. The operator then must activate an unlocking device in order to permit the clamping tool to then be moved to the open position. A modification of this second embodiment relates to the using of a special form of clamp which has a pair of spaced-apart outwardly extending pins on the exterior surface of the clamp. Each pin is to cooperate within a mating opening formed within the clamping tool. This pin and opening arrangement locks the open clamp in the clamping tool. The spring members are pivotally mounted on support heads. Both upper and lower support heads are identical.

BRIEF DESCRIPTION OF THE DRAWING

FIG. 5 is a front view of the clamping assembly of this invention taken along line 5-13 5 of FIG. 1;

FIG. 6 is a bottom view of the clamping assembly of this invention;

FIG. 7 is a view similar to FIG. 1 but showing the tool closed with the clamp closed about the umbilical cord;

FIG. 8 is a cross-sectional view taken along line 8—8 of FIG. 7;

FIG. 12 is a frontal perspective view of a modified form of second embodiment of clamping tool of this invention showing the clamping tool in the open position cradling both clamping members;

FIG. 13 is a rear perspective view of a modified form of second embodiment of the clamping tool of this invention also showing the clamping tool in the open position cradling both the clamping members;

FIG. 14 is a cross-sectional view taken along line 14—14 of FIG. 12;

FIG. 15 is an exploded perspective view of a portion of the clamping tool of this invention showing the cradling arrangement for one of the clamps supported within the clamping tool of this invention; and FIG. 16 is a side elevational view of the special form of clamp which is employed in connection with the tool of FIGS. 12-15 showing the clamp in the closed position.

DETAILED DESCRIPTION OF THE SHOWN EMBODIMENT

Figure 1:
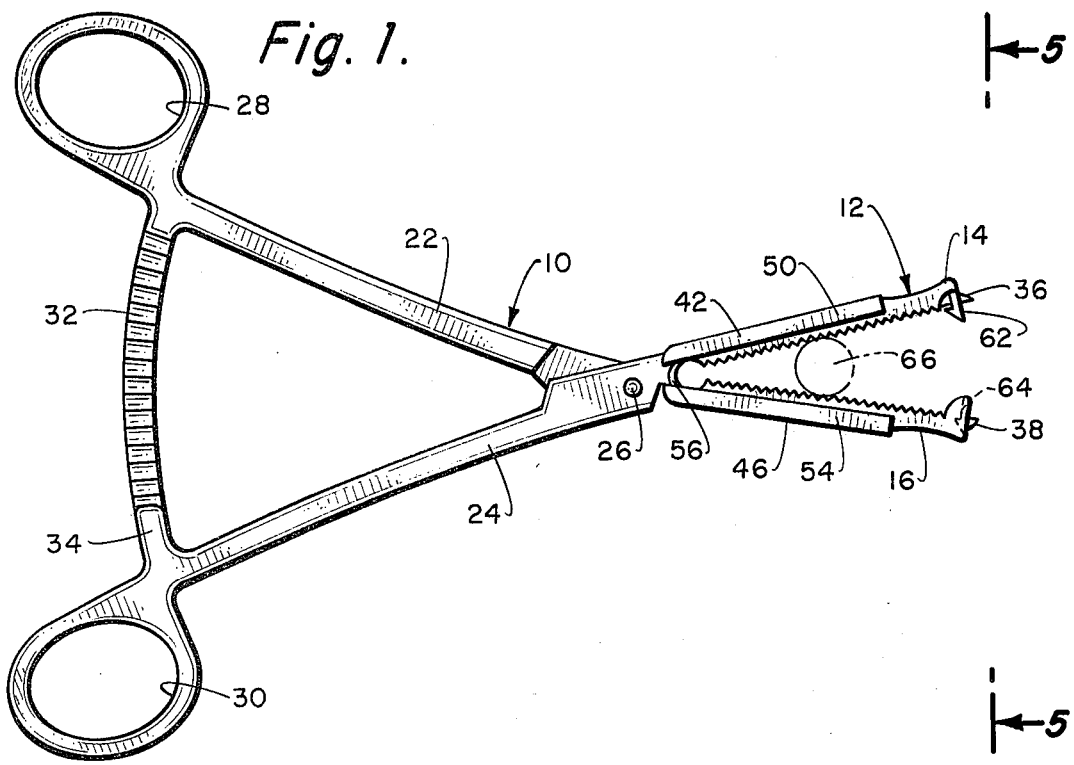
FIG. 1 is a side elevational view of the first embodiment of the clamping assembly of this invention showing the clamping tool in the open position with the umbilical cord clamp installed in place within the tool.
Figure 2:
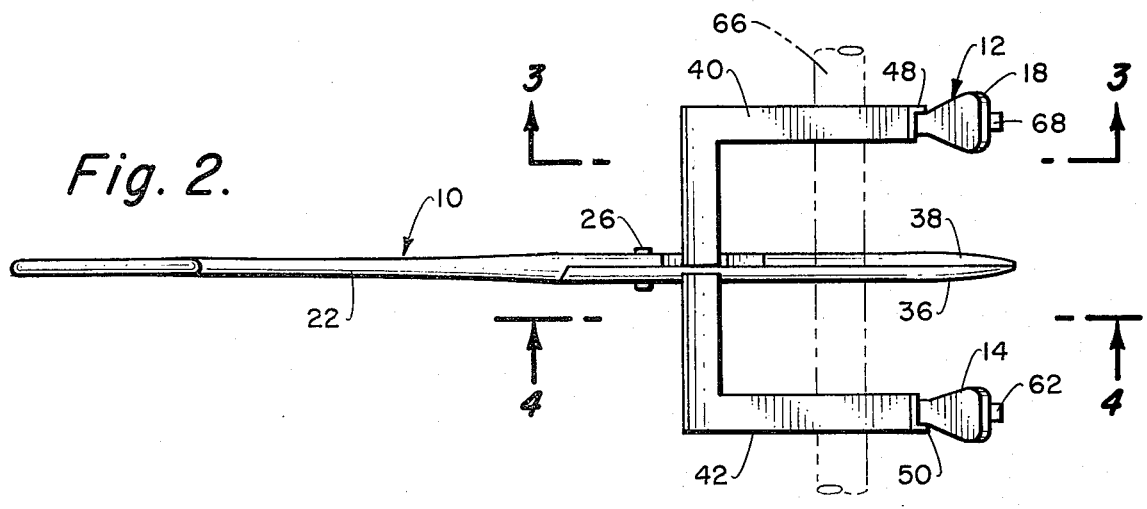
FIG. 2 is a top view of the clamping assembly of FIG. 1.
Figure 3:
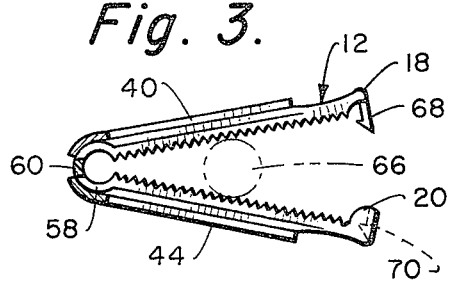
FIG. 3 is a partial cross-sectional view of a portion of the head of the clamping tool taken along line 3—3 of FIG. 2.
Figure 4:
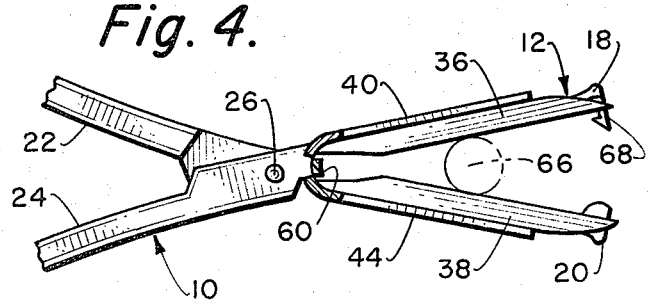
FIG. 4 is a partial cross-sectional view through the head of the tool employed as part of this invention taken along line 4—4 of FIG. 2.

The first embodiment of structure of this invention provides for a system consisting of a reusable surgical stainless steel tool 10 and a plastic disposable clamp assembly 12. The clamp assembly 12 is composed basically of an identical pair of arms 14 and 16 and arms 18 and 20. The purpose of the system of this invention is to clamp both the proximal and distal ends of the umbilical cord and to sever the umbilical cord between the two sets of arms as a one step, one hand procedure.

The purpose of the tool 10 is to hold the disposable clamp assembly 12 and make such immediately available for use. The tool 10 is basically a scissors and is composed of members 22 and 24 which are pivotally connected together through a pivot joint 26. The back end of the member 22 includes a thumb receiving opening 28 and the back end of the member 24 includes a finger receiving opening 30. Adjacent the opening 28 is a ratchet bar 32 which includes a plurality of locking recesses. Adjacent the opening 30 and formed integral with the member 24 is a latching bar 34. The latching bar 34 cooperates with the ratchet bar 32 to lock the tool 10 in any established position. The use of such a ratchet arrangement is deemed to be conventional.

The front end of the member 24 includes a shearing member 36. Also, a shearing member 38 is formed integral with the member 22. The shearing members 36 and 38 cooperate in a conventional manner to form a cutting action substantially identical to a pair of scissors.

Attached to the member 36 and located adjacent the pivot joint 26 are a pair of L-shaped arms 40 and 42. Similarly, a pair of L-shaped arms 44 and 46 are secured to and extend on opposite sides of the shearing member 38. Each of the arms 40, 42, 44 and 46 have a short side flange 48, 50, 52 and 54 attached thereto, respectively.

The cooperation of the clamp assembly 12 with the tool 10 is as follows: The clamp assembly 12 is placed within the head of the tool 10 so that arm 14 is in abutting contact with the side flange 50 of the arm 42. Also, the arm 16 is in abutting contact with the side flange 48 and the arm 20 in abutting contact with the side flange 52. The arms 14 and 16 are joined together by a slightly enlarged loop 56 of plastic material which is integral with arms 14 and 16. It is to be noted that the inside of each of the arms 14 and 16 is formed to include a biting serrated surface.

Similarly, the arms 18 and 20 are integrally joined together by a slightly enlarged loop 58. It is to be noted that the arms 14 and 16, as well as arms 18 and 20, are constructed of a plastic material that is rigid but is flexible to a certain amount. The flexibility is such that if an item such as a pencil was placed between the members 14 and 16 and the members 14 and 16 closed, the members 14 and 16 would readily bend about the pencil. Numerous types of plastic material can be employed to achieve this result.

The loops 56 and 58 are joined together by an elongated thin plastic strip 60. The function of the strip 60 is to maintain the spacing between the pair of arms constant so that the clamp assembly 12 can be just merely inserted within the tool 10 thereby not requiring any adjustment.

The forwardmost edge of the member 14 includes a latching member 62. The latching member 62 is to cooperate within a latching recess 64 formed within the outermost edge of the member 16 when the arms 14 and 16 are in a closed position. Therefore, the arms 14 and 16 are maintained in this closed position when the members 14 and 16 are clamped about the umbilical cord 66.

A similar latching member 68 is formed upon the outermost edge of the member 18 and a similar latching recess 70 is formed on the outermost edge of the member 20.

The operation of the first embodiment 10 of this invention is that the clamp assembly 12 is placed within the head of the tool 10 with the tool 10 in the open position as shown in FIG. 1 of the drawings. The clamp assembly 12 is also in the open at rest position as generally depicted in FIG. 1 of the drawings. This clamp assembly is then maintained in cooperation with the tool 10 until it is desired to employ the use of the tool 10.

At the time it is desired to employ the use of the tool 10 cooperating with the openings 28 and 30. The operator then places the umbilical cord 66 between both of the arms 14 and 16 and 18 and 20. The operator then closes the tool 10 to the position substantially as shown in FIG. 7 of the drawings. In this position, the latching members 62 and 68 cooperate, respectively, with their recesses 64 and 70. Simultaneously with achieving this cooperation, the shearing members 36 and 38 sever the umbilical cord 66 and also the elongated member 60. As a result, the arms 14 and 16 are clamped together and located about the proximal end of the umbilical cord with the arms 18 and 20 clamped together and located about the distal end of the umbilical cord.

The operator then opens the tool 10 which leaves the clamping assembly 12 in a closed position and disassociates the tool 10 from the clamp assembly 12. As a result, the umbilical cord 66 has been severed and a clamp applied to each end of the umbilical cord.

Figure 9:
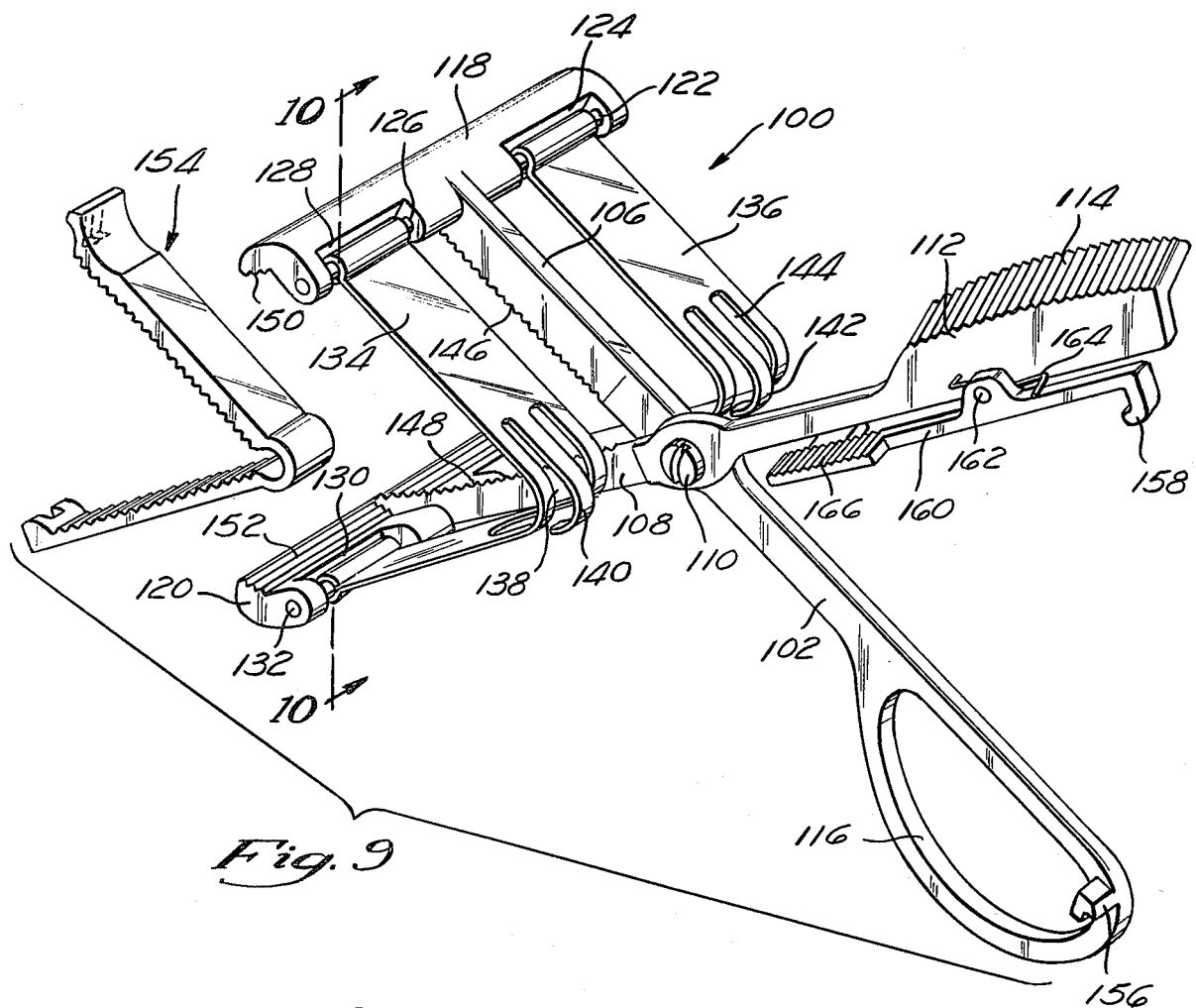
FIG. 9 is a perspective view of the second embodiment of the clamping tool of this invention showing the clamping tool in the open position about to receive one of the pair of clamping members to be clamped about an umbilical cord.
Figure 10:
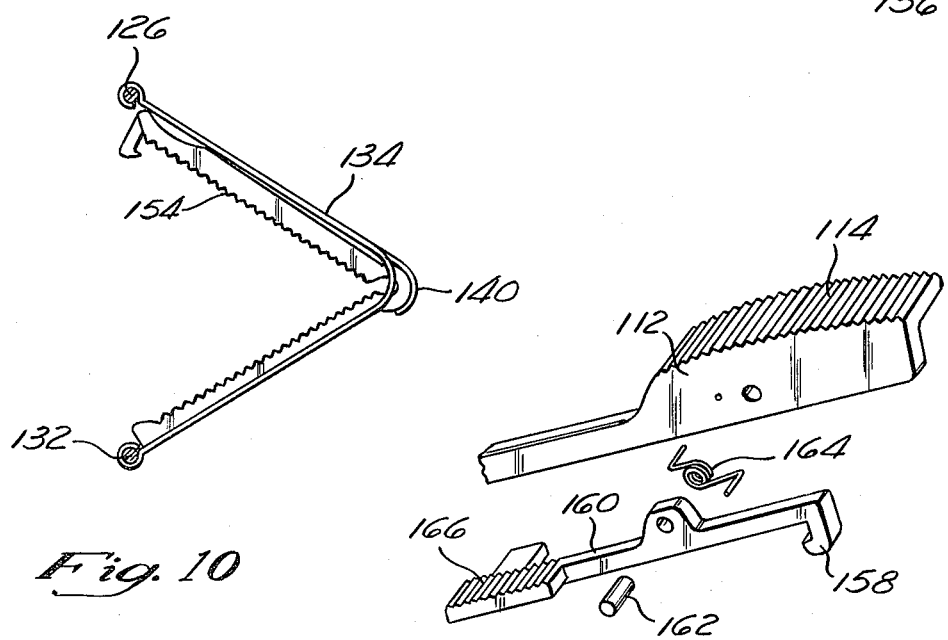
FIG. 10 is a partial cross-sectional view taken along line 10—10 of FIG. 9 showing the cradling of a clamping member within the clamping tool.
Figure 11:
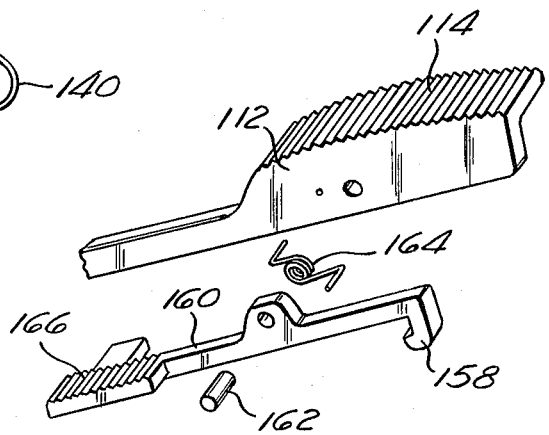
FIG. 11 is an exploded perspective view of the unlocking device incorporated within the clamping tool of this invention to unlock the clamping tool when located in the completely closed position.

Referring particularly to FIGS. 9-11, there is shown the second embodiment 100 of this invention. The second embodiment 100 operates precisely in the same manner as the first embodiment 10 and is to include a pair of pivotally connected scissor members 102 and 104 which is to cause shearing movement between the shearing members 106 and 108. The shearing member 106 is integrally formed as part of the scissor 102 with the shearing member 108 being integrally formed as part of the scissor member 104. The pivotal connection between the members is provided through a bolt assembly 110.

The back end of the member 104 is to include a flattened section 112 which includes a serrated surface 114. The serrated surface is to be contacted by the palm of the doctor's hand. The fingers of the doctor's hand are to be conducted through an enlarged opening 116 which is formed within the outer end of the member 102. Therefore, it can be seen by manually compressing together the members 102 and 104, the tool 100 of this invention is to be operated.

The outer end of the shearing member 106 includes a transverse elongated member 118. A member 120, which is basically a mirror image of member 118, is attached to the outer end of the shearing member 108.

Within member 118, on one side of the shearing member 106, there is mounted a pin 122 located within a cut-out section 124. On the other side of the shearing member 106, a similar pin 126 is mounted within a cut-out section 128.

In a similar manner, a pair of cut-out sections are located within the member 120 with only cut-out section 130 being shown. Within the cut-out section 130 is located a pin 132.

A V-shaped spring member 134 is pivotally mounted between the pins 126 and 132. Similarly, an identical spring member 136 is pivotally mounted between pin 122 and the pin (not shown) mounted on the member 120. The spring members 134 and 136 assume an at rest position tending to hold the tool 100 in the open position as is shown in FIGS. 9 and 10 of the drawings. The spring members 134 and 136 are to be constructed of a sheet metal material and will usually be of stainless steel.

The apex of the V-shaped spring member 134 includes a cut-out section 138. This cut-out section 138 has caused the formation of an outwardly protruding stop member 140. A similar stop member 142 is formed by the cut-out section 144 of the spring member 136. The purpose of the stop members 140 and 142 will be explained further on in the specification.

It is to be noted that the shearing members 106 and 108 include respective cutting edges 146 and 148. The cutting edges 146 and 148 are serrated so as to facilitate cutting of the umbilical cord. The serrating of the edges 146 and 148 also tends to prevent slipping of the umbilical cord outwardly from between the spring members 106 and 108.

The member 118 includes a serrated recessed inner surface 150. A similar serrated inner surface 152 is formed on the inside of the member 120. A clamp member 154, which is basically similar to the previously described clamp assembly 12 with the exception that there is no thin plastic strip 60, is to be located or cradled within the spring member 134 such that the apex of the clamp member 154 is located within the cut-out section 138 in abutting contact with the stop 140. The free ends of the clamp member 154 are in turn located within the inner surfaces 150 and 152. It is to be understood that a similar clamp member (not shown) is to be cradled within the spring member 136 in a similar manner. It is to be further understood that the clamp members 154 are deemed to be conventional and form no specific part of this invention, such being in relatively common use at the present time.

It should be readily apparent that with the clamp members 154 located cradled within their respective spring member 134 and 136, that the apex section of each clamp member is held in place due to cooperation within the respective cutout sections 138 and 144. The free ends of each of the clamp members 154 are also slightly pressed against the inner sections 150 and 152. Therefore, as a result, the clamp members 154 are securely held in place and accidental dislodgement from the tool 100 is prevented.

The operation of the tool 100 of this invention is in precisely the same manner as the first embodiment and reference is to be had thereto. As the tool 100 is closed, each of the clamp members 154 are to clamp on a section of the umbilical cord. The clamp members 154 will naturally tend to bow about the umbilical cord since the members 154 are constructed of a bendable plastic material. This bowing of the members 154 is accommodated since the sheet metal spring members 134 and 136 are also capable of bowing. The clamping force is applied directly to the outer end of the clamp members 154 to secure the outer ends together and securely lock the clamp members 154 about the umbilical cord.

It is extremely important that both the umbilical cord clamp members 154 secure to its respective section of umbilical cord at the time the umbilical cord is severed by the shearing action of shearing members 106 and 108. If, per chance, the clamp members 154 are not locked together, then the severed umbilical cord will cause excessive bleeding from both the mother and the child. Therefore, some means is desirable to insure that the clamp members 154 are locked in place. This means takes the form of a female latch member 156 which is secured to the back end of the member 102. A male latch member 158 is integrally formed in conjunction with a latching bar 160. The latching bar 160 is pivotally mounted by means of a pivot pin 162 to the scissor member 104. The pin 162 is encircled by a spring 164 which exerts a continuous bias on the bar 160 locating such in the position shown within FIG. 9 of the drawings. The forward end of the latching bar 160 includes an enlarged section 166.

When the operator has completely closed the tool 100 and the clamp members 154 are insured of being tightly latched together, the male latch member 158 engages the female latch member 156. This informs the operator that the latch members 154 are locked together. The operator then only need to press against enlarged section 166 of the bar 160 which then causes the bar 160 to pivot slightly and disengage the latch member 158 from the latch member 156. This then permits the tool 100 to be moved to the open position as shown within FIG. 9.

Referring particularly to FIGS. 12–15, there is shown a modified form of clamping tool 200 which operates precisely in the same manner as both the first embodiment and the second embodiment of this invention. The clamping tool 200 includes a pair of pivotally connected together scissor members 202 and 204 which produce the shearing action between the shearing members 206 and 208. Shearing member 206 is integrally attached to the scissor member 204 and shearing member 208 is integrally attached to scissor member 202. The pivotal connection between the members 202 and 204 is provided through a bolt assembly 210.

The back end of the member 202 includes a flattened section 212 which is to be contacted by the palm of the doctor's hand. The fingers of the doctor's hand are to be conducted through the enlarged opening 214 which is formed within the outer end of the member 204. Therefore, it can be seen by manually compressing together the members 202 and 204 that the tool 200 of this invention is to be operated, part of the operation of which causes shearing action by the shearing members 206 and 208. These members 206 and 208 are to effect cutting of the umbilical cord.

The outer end of the shearing member 206 has attached thereto a transverse elongated member 216. A transverse elongated member 218, which is an exact mirror image of member 216, is secured to the outer end of the shearing member 208.

One end of a V-shaped spring member 220 is pivotally attached by pivot pin 222 to the transverse elongated member 216. The opposite end of the V-shaped spring member 220 is pivotally attached by pivot pin 224 to the transverse elongated member 218. Spring member 220 is located on one side of the shearing members 206 and 208. On the opposite side of the shearing members 206 and 208 is a second V-shaped spring member 226 which is attached in precisely the same manner as member 220 to the transverse elongated members 216 and 218.

It is to be noted that the apex section of the spring member 220 has formed therein a hole 228. A similar hole (not shown) is formed within the spring member 226 in the same location. The function of the holes will be explained further on in the specification.

Formed within the transverse elongated member 216 are recesses 230 and 232. Recess 230 is located on one side of the shearing member 206, with recess 232 located on the opposite side of the shearing member 206. In a similar manner, formed within the transverse elongated member 218 are recesses 234 and 236. Connecting with each recess 230, 232, 234, 236 is a hole 238. It is to be understood that there will be a separate hole 238 for each recess. The function of each of the holes 238 will again be discussed further on in the specification.

The clamping tool 200 is designed to be employed with a specific form of plastic disposable clamp 240. The clamp 240 is similar to previously described clamp 12 in which it includes a pair of arms 242 and 244, the inner edges of which respectively are formed into serrated surfaces 246 and 248. The arms 242 and 244 are connected together through an apex section 250. The outer end of the arm 242 is formed into a bendable hook 252 with the outer end of the arm 244 being formed into a catch 254. The exterior surface of the apex section 250 has attached thereto a pin 256. Formed on the exterior surface of the arm 244 adjacent the catch 254 is a pin 258.

The clamp 240 is initially located in the open condition shown within FIGS. 12–15. A nurse, or other personage, is to take a clamp 240 and insert such within the clamping tool 220 as shown within the drawing so that pin 256 cooperates within the opening 228 and the pin 258 cooperates within a hole 238. There are to be two separate clamping members 240 installed within the clamping tool 200. Because the transverse elongated members 216 and 218 are identical, it does not make any difference whether the clamp 240 is right-side-up or upside-down. In other words, the pin 258 will cooperate with a hole within either the transverse elongated member 216 or member 218. The purpose of the pins 258 and 256 is so as to laterally stabilize the clamp 240 when installed within the clamping tool 200 and prevent accidental dislodgement therefrom. It is to be noted that the clamp 240 will be slightly compressed when installed within clamping tool 200. This means that the inherent outwardly biasing movement of the clamp 240 will tend to maintain the clamp 240 in connection with the clamping tool 200.

When the clamping tool 200 is operated to effect closing of the clamps 240, the umbilical cord is to be located between the serrated surfaces 246 and 248. The clamp 240 will be bowed about the umbilical cord which is not shown within FIG. 16. The rearwardmost tooth 260 of the serrated surface 248 is substantially enlarged. The reason for this is that it is not desired for the umbilical cord to extend within the interior of the apex section 250. It is desired for the umbilical cord to be tightly clamped. Therefore, it would be preferred if the umbilical cord did not extend within the apex section 250.

As previously described in relation to the previous embodiment, once the clamping action is initiated, it is desired to continue until each hook section 253 engages firmly with its respective catch 254. For this purpose, there is provided a ratchet bar 264 which is fixedly secured to the member 202. The ratchet bar 264 connects with an opening 266 formed within the member 204. A ratchet wheel 268 is pivotally mounted upon the member 204 within the opening 266. A spring 270 is connected to the ratchet wheel 268 and is mounted within the member 204.

The ratchet wheel 268 is under a continuous bias by the spring 270 to a particular position. When the ratchet wheel 268 is engaged by the ratchet bar 264, movement overcenter from this position is prevented and once the ratchet wheel 268 engages a particular tooth of the ratchet bar 24, movement only in the closing direction is permitted (opening movement of the clamping tool not being permitted). It is to be understood that the ratchet wheel 268 has a protruding pawl which is to engage with a tooth of the ratchet bar 264.

Once the clamping tool 200 has been completely closed and it is assured that each of the hooks 252 are engaged with their respective catches 254, the latching pawl of the ratchet wheel 268 will fall within recess 272 of the ratchet bar 264. This permits the ratchet wheel 268 to move over-center and permit the clamping tool to be opened to the completely open position. When the clamping tool 200 is in the completely open position, the spring 270 will cause the ratchet wheel 268 to move back to its at-rest position, which is no longer overcenter. In this particular position, the latching pawl 268 is again ready to engage with the ratchet bar 264 and permit only closing movement of the clamping tool 200.

It is to be noted that when "loading" the clamp 240 within the clamping tool 200, the nurse or operator only needs to slide clamp 240 into its appropriate position within the recesses 230 and 234 and also recesses 232 and 236. The forward lip of each of the recesses is slightly raised, as is clearly shown within FIGS. 14 and 15. When each clamp 240 is fully installed, as is shown within FIG. 14, the outermost edges of the arms 240 and 242 rest behind the shoulder section of its appropriate recess. This means that the clamp 240 "snaps" into place so that the operator will know when the clamp 240 is properly installed within the clamping tool 200.

What is claimed is:

1. In combination with a first clamp having a first set of arms connected together in a generally V-shaped arrangement and a second clamp having a second set of arms connected together in a general V-shaped arrangement, both said sets of arms being movable between an open position and a closed position, with said arms about an umbilical cord and in said closed position there being a fastening assembly attached to the free end of said arms to tightly lock together said arms in said closed position, an umbilical cord clamping tool to simultaneously lock together said first and second clamps, said umbilical cord clamping tool comprising:

a pair of cutting members pivotally connected together in a scissor-like manner, each of said cutting members including a cutting blade, said cutting blades being adapted to cooperate together to facilitate cutting of an umbilical cord;

the outermost end of one of said cutting members being fixedly attached to a first transverse member with the outermost end of the other of said cutting members being fixedly attached to a second transverse member;

a first substantially V-shaped spring member terminating in a pair of first ends, one of said first ends being pivotally attached to said first transverse member, the other said first end being pivotally attached to said second transverse member, a second substantially V-shaped spring member terminating in a pair of second ends, one of said second ends being pivotally attached to said first transverse member, the other said second end being pivotally attached to said second transverse member, said first V-shaped spring member being located on one side of said pair of cutting members with the other said V-shaped spring member being located on the other side of said cutting members, said first and second V-shaped spring members exert a continuous bias on said pair of cutting members to locate such in an open position to receive said first and second clamps in their said open position;

said first clamp to be cradled within said first V-shaped spring member with said second clamp to be cradled within said second V-shaped spring member, both said first V-shaped spring member and said second V-shaped member being capable of bowing outwardly during the scissors movement of said cutting members to a closed position resulting in locking together of said first clamp and said second clamp and locate such in their said closed position, said bowing outwardly to accommodate the inherent enlargement of said first and second clamps about the umbilical cord; and means for seating and laterally restraining both said first clamp and said second clamp within its respective said V-shaped spring member.

2. The combination as defined in claim 1 wherein:

said means comprising a mating assembly of pins and holes, said pins being mounted on each said clamp, said holes being formed within said clamping tool.

3. The combination as defined in claim 2 wherein:

said clamping tool including locking means which becomes interlocked when said clamping tool begins its movement from said open position toward said closed position, said locking means only becoming disengaged when said clamping tool reaches said closed position.

* * * * *